(12) United States Patent
Di Matteo et al.

(10) Patent No.: US 9,910,005 B2
(45) Date of Patent: Mar. 6, 2018

(54) BIOSENSOR

(71) Applicant: STMicroelectronics S.R.L., Agrate Brianza (IT)

(72) Inventors: Andrea Di Matteo, Naples (IT); Vincenza Di Palma, Cimitile (IT); Maria Fortuna Bevilacqua, Sant'Agata de Goti (IT); Angela Cimmino, Caserta (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 71 days.

(21) Appl. No.: 14/951,136

(22) Filed: Nov. 24, 2015

(65) Prior Publication Data

US 2016/0077034 A1 Mar. 17, 2016

Related U.S. Application Data

(62) Division of application No. 13/929,654, filed on Jun. 27, 2013, now Pat. No. 9,244,067.

(30) Foreign Application Priority Data

Jul. 10, 2012 (IT) ................ VI2012A0166

(51) Int. Cl.
| | | |
|---|---|---|
| *G01N 27/28* | (2006.01) | |
| *C12Q 1/00* | (2006.01) | |
| *G01N 33/543* | (2006.01) | |
| *G01N 27/327* | (2006.01) | |
| *G01N 27/403* | (2006.01) | |
| *G03F 7/00* | (2006.01) | |
| *G03F 7/16* | (2006.01) | |
| *G03F 7/20* | (2006.01) | |
| *G03F 7/26* | (2006.01) | |

(52) U.S. Cl.
CPC ............ *G01N 27/28* (2013.01); *C12Q 1/001* (2013.01); *G01N 27/327* (2013.01); *G01N 27/403* (2013.01); *G01N 33/54386* (2013.01); *G03F 7/0035* (2013.01); *G03F 7/16* (2013.01); *G03F 7/20* (2013.01); *G03F 7/26* (2013.01)

(58) Field of Classification Search
CPC ............ G01N 27/28; G01N 33/54386; G01N 27/327; G01N 27/403
See application file for complete search history.

(56) References Cited

U.S. PATENT DOCUMENTS 5,444,234 A 8/1995 Hennerici et al.
6,281,006 B1 8/2001 Heller et al.
(Continued)

OTHER PUBLICATIONS

Allock et al., "Ultraviolet Photolithographic Development of Polyphosphazene Hydrogel Microstructures for Potential Use in Microarray Biosensors," *Chem. Mater.* 18:609-613, 2006.
(Continued)

*Primary Examiner* — Melanie Y Brown
(74) *Attorney, Agent, or Firm* — Seed IP Law Group LLP

(57) ABSTRACT

A biosensor includes a flexible foil with an electrode layer positioned on the foil. An adhesive layer is positioned on the foil layer, and a first photo-definable hydrogel membrane is positioned over the electrode layer and the adhesive layer. A second photo-definable hydrogel membrane with an immobilized bio-recognition element is positioned over the first hydrogel membrane in contact with the electrode layer through an opening in the first hydrogel membrane.

20 Claims, 3 Drawing Sheets

(56) References Cited

U.S. PATENT DOCUMENTS 6,485,703 B1 11/2002 Coté et al.
2006/0219294 A1 10/2006 Yabuuchi et al.
2009/0101498 A1 4/2009 Papadimitrakopoulos et al.

OTHER PUBLICATIONS

Arkles et al., *Silanes and Other Coupling Agents*, VSP, Bristol, Pennsylvania, 1992, "Factors contributing to the stability of alkoxysilanes in aqeous solution," pp. 91-104.

Brahim et al., "Electroconductive Hydrogels: Electrical and Electrochemical Properties of Polypyrrole-Poly(HEMA) Composites," *Electroanalysis* 17(7):556-570, 2005.

Campomanes et al., "Study of conductivity of polypyrrol-poly(vinyl alcohol) composites obtained photochemically," *Synthetic Metals* 102:1230-1231, 1999.

Fedorovich et al., "The effect of photopolymerization on stem cells embedded in hydrogels," *Biomaterials* 30:344-353, 2009.

Jang et al., "Three-Dimensionally-Patterned Submicrometer-Scale Hydrogel/Air Networks That Offer a New Platform for Biomedical Applications," *Nano Letters* 8(5):1456-1460, 2008.

Li et al., "Photopolymerization of HEMA/DEGDMA hydrogels in solution," *Polymer* 46:11540-11547, 2005.

Liu et al., "Three-Dimensional Photopatterning of Hydrogels Containing Living Cells," *Biomedical Microdevices* 4(4):257-266, 2002.

Mugweru et al., "Electrochemical Redundant Microsensor Arrays for Glucose Monitoring with Patterned Polymer Films," *Electroanalysis* 19(4):453-458, 2007.

Odaci et al., "In Situ synthesis of biomolecule encapsulated gold-cross-linked poly(ethylene glycol) nanocomposite as biosensing platform: A model study," *Bioelectrochemistry* 79:211-217, 2010.

Schmedlen et al., "Photocrosslinkable polyvinyl alcohol hydrogels that can be modified with cell adhesion peptides for use in tissue engineering," *Biomaterials* 23:4325-4332, 2002.

Yan et al., "Immobilizing Enzymes onto Electrode Arrays by Hydrogel Photolithography to Fabricate Multi-Analyte Electrochemical Biosensors," *ACS Applied Materials & Interfaces* 2(3):748-755, 2010.

Yang et al., "Synthesis of Photoacid crosslinkable hydrogels for the fabrication of soft, biomimetic microlens arrays," *J. Mater. Chem.* 15:4200-4202, 2005.

Yu, "The development of photolithography process for pentacene active layer," SMDL Annual Report, School of Electrical Engineering, Seoul National University, 2002.

Yu et al., "Use of hydrogel coating to improve the performance of implanted glucose sensors," *Biosensors and Bioelectronics* 23:1278-1284, 2008.

Mugweru, A. et al., "Electrochemical Sensor Array for Glucose Monitoring Fabricated by Rapid Immobilization of Active Glucose Oxidase within Photochemically Polymerized Hydrogels," Journal of Diabetes and Technology 1(3):366-371, May 2007.

Urban, G. et al., "Miniaturized multi-enzyme biosensors integrated with pH sensors on flexible polymer carriers for in vivo applications," Biosensors & Bioelectronics, vol. 7, pp. 733-739, 1992.

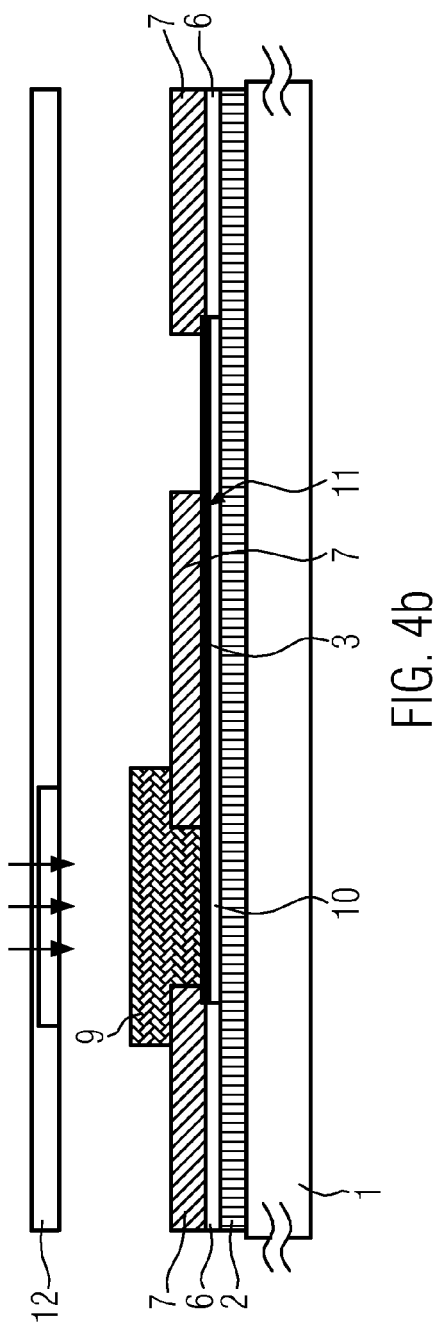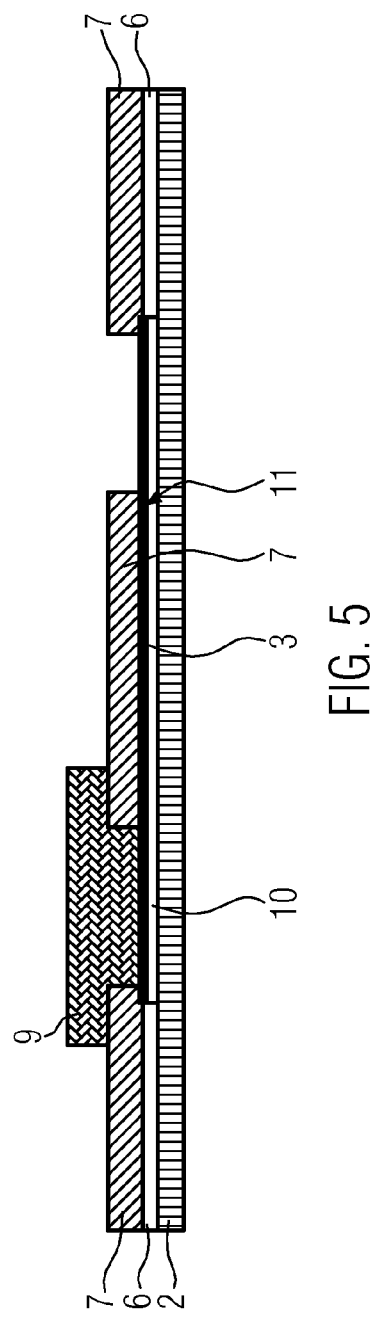

BIOSENSOR

BACKGROUND

Technical Field

The present disclosure relates to the field of biosensors and, in particular, to the immobilization of bio-recognition elements as, for example, cell receptors, enzymes, antibodies or nucleic acids, on sensor surfaces, in particular on flexible foils, by means of hydrogels.

Description of the Related Art

A biosensor is a device for the detection of an analyte. A biosensor comprises a bio-recognition element (sensitive biological element) and a detector element that transforms a signal resulting from the interaction of the analyte with the biological element into another signal that can be more easily measured and quantified. Immobilization of the bio-recognition element can be attained by passive adsorption, covalent binding via suitable linker chemistry and entrapment within hydrogel matrices or solid polymers and by inclusion in layers obtained by fusion of vesicles.

Hydrogels are especially attractive materials for fabricating electrochemical biosensing because a hydrated gel provides an excellent matrix encapsulation of functional enzymes, vaccine and cell sequestration and metabolite detection. In particular, the soft and hydrated environment of a swollen hydrogel can provide proteins with near-physiological conditions that minimize denaturation and help them to carry out their full biological functions. The three-dimensional geometry of hydrogels enables them to contain a much larger quantity of sensing reagent, thereby increasing their signal-to-noise ratio and sensitivity. Hydrogel photo-definable membranes have been introduced for providing immobilization of bio-recognition elements.

BRIEF SUMMARY

According to an embodiment, a biosensor is provided, comprising a foil, for example, a flexible polymeric foil;

an electrode layer (being part of an electrochemical sensor) above the foil;

a first photo-definable hydrogel membrane without bio-recognition element arranged partly above the electrode layer and partly directly on the foil; and a second photo-definable hydrogel membrane with an immobilized bio-recognition element above the electrode layer, particularly, provided partly on the electrode layer in direct contact with the same.

The bio-recognition element can be any sensitive biological element known in the art, for example, a cell receptor, an enzyme, an antibody or a nucleic acid.

In contrast to the known art, two photo-definable hydrogel membranes are provided, in accordance with an embodiment, one of which (the first membrane) is formed on the foil and provides structural rigidity and reliable adhesion whereas the other one (the second bioactive membrane) is formed above the electrode, particularly, directly on the portion of the electrode layer that is not covered by the first photo-definable hydrogel membrane and provided for the sensing property by the included bio-recognition element. The second photo-definable hydrogel membrane can be arranged partly on and in direct contact with the first photo-definable hydrogel membrane and partly on and in direct contact with the electrode layer. In particular, the first photo-definable hydrogel membrane may expose a portion of the electrode layer and, in this case, the second photo-definable hydrogel membrane is formed directly on and in contact with the electrode layer and partly covering the first photo-definable hydrogel membrane. By the term photo-definable it is generally denoted that the membranes can be structured/patterned by irradiation, for example, UV irradiation, in particular, in the context of lithography.

Particularly, the second photo-definable hydrogel membrane may be a biocompatible matrix for encapsulation of bio-recognition enzymes that can be patterned on electrodes by lithographic technology. The second photo-definable hydrogel membrane may have the property of photo-cross-linking of a soluble polymer via photo-reactive side groups of the polymer or via addition of photo-sensitizer or photo-initiator into a polymer network or gel. Immobilization by cross-linking yields carriers in which no covalent bonds to the enzyme are formed. The enzyme can be physically entrapped within the bulk of a polymer or in the mesh of a swollen polymer network.

In one embodiment, the biosensor further comprises an adhesive layer arranged on the foil and between a part of the first photo-definable hydrogel membrane and the foil. The adhesive layer can be provided in order to enhance the structural rigidity/integrity of the biosensor. For example, a silane composition of the adhesive layer is suitable.

Problems related to imobilization and adhesion are also addressed by a method for the manufacture of a biosensor, comprising the steps of providing a foil, for example, a flexible polymeric foil;

forming an electrode layer over the foil;

forming a first photo-definable hydrogel membrane without bio-recognition element partly over the electrode layer and partly directly on the foil;

forming a second photo-definable hydrogel membrane with an immobilized bio-recognition element above the electrode layer.

According to an example, the step of forming the first photo-definable hydrogel partly over the electrode layer comprises the subsequently performed steps of depositing a first photo-definable hydrogel material directly on the electrode layer and lithographically patterning the first photo-definable hydrogel material to expose a portion of the electrode layer (that will actually work as a sensing electrode in the finished product).

The step of forming the second photo-definable hydrogel membrane with a bio-recognition element above the electrode layer may comprise the subsequently performed steps of depositing a second photo-definable hydrogel material directly on the first photo-definable hydrogel membrane and directly on the portion of the electrode region exposed by the first photo-definable hydrogel membrane;

exposing only the region of the second photo-definable hydrogel material directly deposited on the portion of the electrode region exposed by the first photo-definable hydrogel membrane to radiation; and removing the region of the second photo-definable hydrogel material that was not exposed to the radiation.

Alternatively, the step of forming the second photo-definable hydrogel membrane with a bio-recognition element above the electrode layer may comprise the subsequently performed steps of forming a second photo-definable hydrogel material only directly on the portion of the electrode region exposed by the first photo-definable hydrogel membrane and partly overlapping the first photo-definable hydrogel membrane and exposing the second photo-definable hydrogel material to radiation.

According to an example, the electrode layer is formed on a part of the foil and the method further comprises the steps of forming an adhesive layer on portions of the foil that are not covered by the electrode layer and forming the first photo-definable hydrogel membrane on the adhesive layer.

In all of the above-mentioned examples, the electrode layer may be formed on a part of the foil and further the steps of forming an adhesive layer on portions of the foil that are not covered by the electrode layer and forming the first photo-definable hydrogel membrane on the adhesive layer may be performed.

The adhesive layer may be formed on a silane basis. The formation of the silane adhesive layer may comprise the subsequently performed steps of plasma treating, in particular, $O_2$ plasma treating, the foil (with the electrode layer present);

immersing the foil in a silane solution (prepared by hydrolysis and condensation of silane-oligomers, for example);

rinsing the foil in a solvent; and forming a reliable foil-silane bond by heating the foil with the silane adhesive layer.

These steps may be performed in presence of a photoresist formed on the electrode layer in order to protect the electrode layer during the process of forming the adhesive layer. In this case, the photoresist is removed by a suitable solvent after heating the foil with the silane adhesive layer.

BRIEF DESCRIPTION OF THE SEVERAL VIEWS OF THE DRAWINGS

Features and advantages of various embodiments will be described with reference to the drawings. In the description, reference is made to the accompanying figures that illustrate embodiments or portions thereof. It is understood that such embodiments do not represent the full scope of the invention.

FIG. 4b illustrates a state of processing of a biosensor according to the example of FIG. 1, wherein a second photo-definable hydrogel membrane with an immobilized bio-recognition element is formed according to a second alternative.

FIG. 5 illustrates a state of processing of a biosensor according to the example of FIG. 1, after removal of a support substrate.

DETAILED DESCRIPTION

Figure 1:
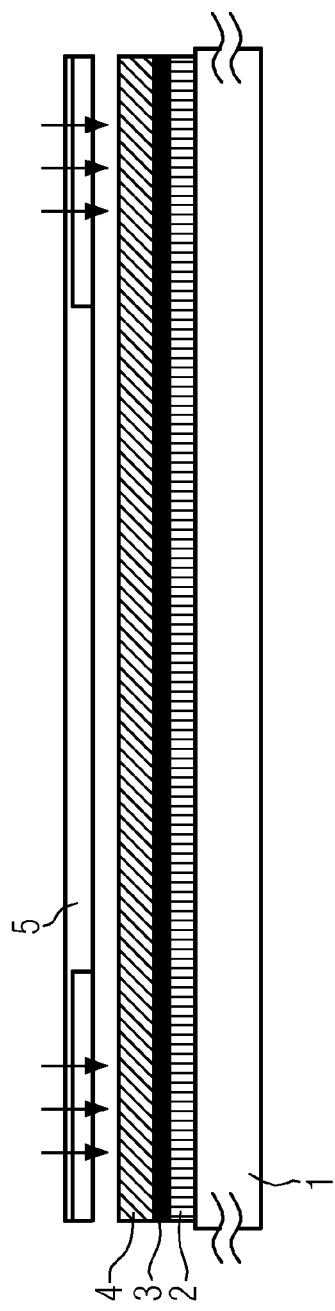
FIG. 1 illustrates a state of processing of a biosensor according to an embodiment, wherein an electrode layer is formed.

Despite recent engineering progress in the field of biosensors, the inventor has recognized that there is still a need for providing biosensors with improved immobilization of biorecognition elements, in particular, in the context of miniaturization and the integration with silicon based electronic devices, electrode layers, etc. Moreover, in the case of hydrogel photo-definable membranes, adhesion to flexible foils or other substrates has proven poor in practice.

A biosensor according to one embodiment of the present disclosure comprises a foil. The foil may be a flexible polymeric foil, for example, made of or comprising PET (polyethylene terephthalate), PEN (polyethylene naphthalate), PEEK (polyether ether ketone) or PI (polyimide). The biosensor comprises an electrode layer, for example, made of or comprising a metal (for example, gold) or an electrically conductive polymer.

The biosensor comprises a first and a second photo-definable hydrogel membrane. According to different embodiments, the first and the second photo-definable hydrogel membranes can be made of the same material or of different materials. The material of the first photo-definable hydrogel membrane may be chosen with particular consideration of adhesive properties. According to an example, the hydrogel photo-definable membranes are made of water swollen hydrophilic materials that include polymeric chains that are crosslinked together either covalently or not covalently. Their monomers or prepolymers are soluble in water, while the polymers are insoluble in water at physiological temperature, pH value and ionic strength. They will swell to an equilibrium value of 10% to 98% $H_2O$ physiologic temperature, pH value and ionic strength. The water content (% $H_2O$) is defined as % $H_2O=100\times$(weight swollen polymer-weight dry polymer)/weight swollen polymer. The polymers may have molecular weights in the range of 500-200000 dalton, and whose properties, including viscosity, softening temperature and degradation temperature, are optimized according to the specific application.

The hydrogel photo-definable membrane may be composed of a monomer, oligomer or prepolymers (the molecular weight of prepolymer controls mechanical properties and viscosity), or binder which ensure mechanical properties of the mixture (adhesion, chemical strength, etc.); of a solvent which controls a number of the mechanical properties (for example the viscosity of the mixture); and of photo-active materials (PAC) or photoinitiators (PhI).

According to one embodiment, the hydrogel photo-definable membrane behaves like a negative photoresist used in negative photolithographic process, where a water development removes the photoresist portion that was not exposed to irradiation. In this case, the hydrogel photo-definable membrane material containing the precursor monomers or oligomer or prepolymer for exposure to the incident UV radiation, for example, undergoes photo-polymerization and/or photo cross linking reaction. The cross-linking of the membrane determines an increase of its molecular weight, which induces an advantageous diminution of solubility of the membrane in water.

Examples of hydrogel photo-definable membranes composed of simple monomers or a mix of different monomers are:

Neutral

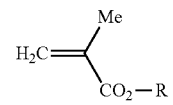

Hydroxyalkyl methacrylates

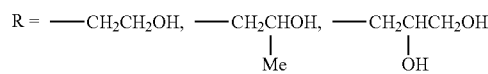

-continued

H$_2$C=CH–CH=CH–CH$_2$OH 2,4-Pentadiene-1-ol

H$_2$C=CR–CO–NR'R''

Acrylamide derivatives
R = —H, Me, R', R'' = —H, Me, Et, —CH$_2$CHOHMe

N-Vinyl Pyrrolidone

Hydrophobic acrylics
R = —H, Me, R' = —Me, Bu, OMe, CN, —OCH$_2$CH$_2$OMe

Acid or Anionic

Acrylic acid derivatives
R = —H, Me

Sodium styrenesulfonate

Basic or Cationic

H$_2$C=CR–CO$_2$–C$_2$H$_4$N–R'R''

Aminoethyl methacrylate derivatives
R, R', R'' = —H, Me, Bu

Vinyl Pyridine

Crosslinkers

Ethylene glycol dimethacrylate derivatives

Methylene-bis-acrylamide

Examples of hydrogel photo-definable membranes composed of oligomers or prepolymers are:

CH$_2$=CH–C(=O)–O–(CH$_2$CH$_2$O)$_n$–C(=O)–CH=CH$_2$
PEG diacrylate

CH$_2$=C(CH$_3$)–C(=O)–O–(CH$_2$CH$_2$O)$_n$–C(=O)–C(CH$_3$)=CH$_2$
PEG diamethacrylate HO–(CH(CH$_3$)–CH$_2$–O–C(=O)–CH=CH–C(=O)–O)$_n$–(CH$_2$CH$_2$O)$_m$–OH
Polypropylene fumarate-co-ethylene glycol Acrylic modified PVA Commutated hyaluronic acid

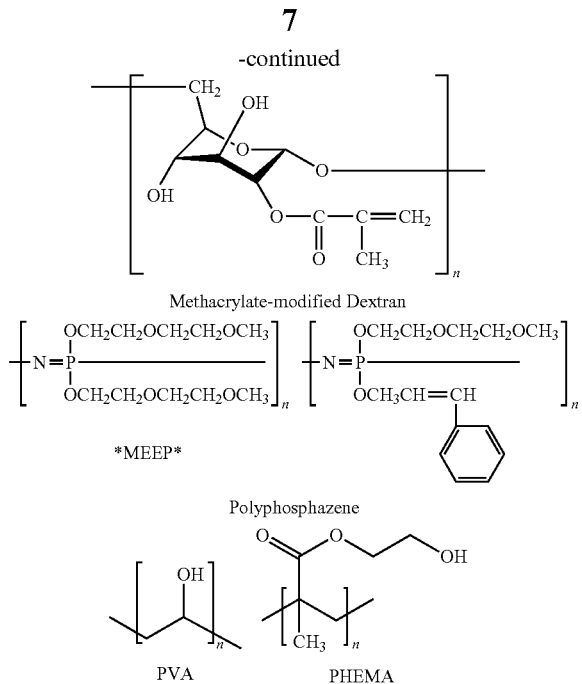

In the following, some examples for the manufacture of the hydrogel photo-definable membranes are given.

Example of polyHEMA poly(2-hydroxyethyl methacrylate): Crosslinked hydrogels were prepared at room temperature by UV-initiated polymerization of HEMA using a photo-initiator and various cross-linkers to adjust the cross-linking density, thus, modifying the swell and mechanical properties of hydrogels.

1. HEMA-DEGDMA. Hydrogel precursors formed by 2-hydroxyethyl methacrylate (HEMA), diethylene glycol dimethacrylate (DEGDMA) as cross-linker.

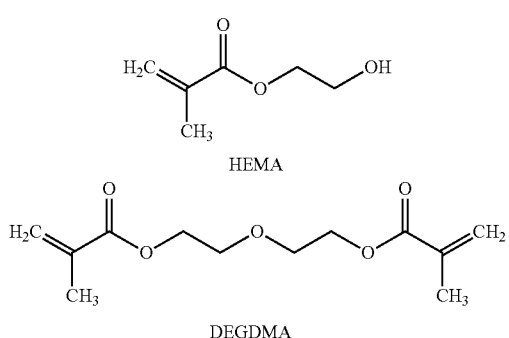

2. HEMA-EGDMA. Hydrogel precursors formed by Hydroxyethyl methacrylate (HEMA,) ethylene glycol dimethacrylate (EGDMA) and a photoinitiator.

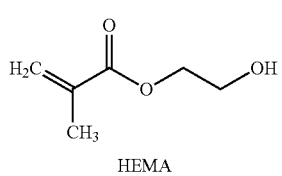

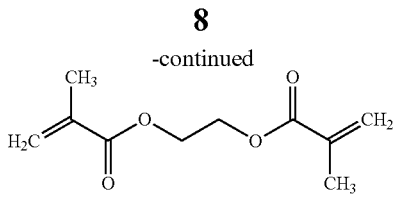

3. PHEMA-co-PMMA Hydrogel precursors formed by poly(2-hydroxyethyl methacrylate-co-methyl methacrylate PHEMA-co-PMMA, photoacid generators and external crosslinkers tetramethoxymethyl glycoluril (TMMGU).

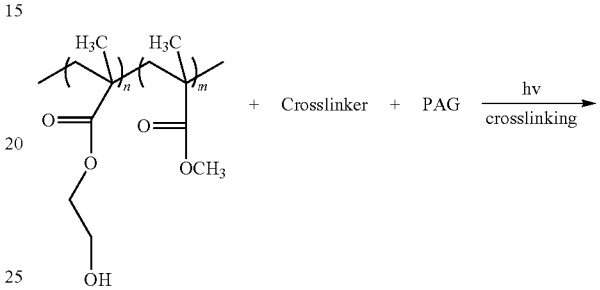

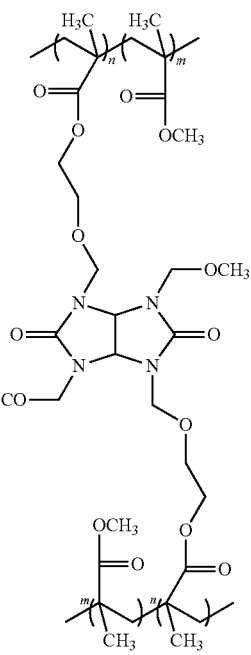

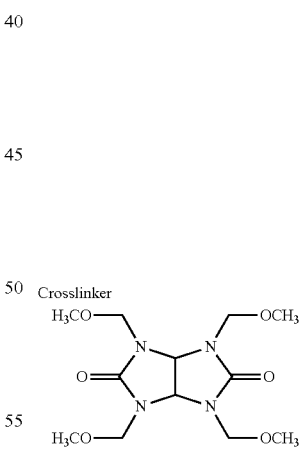

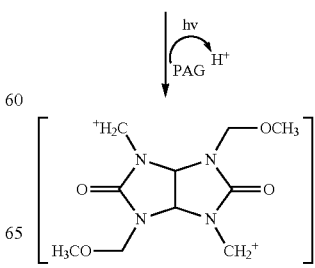

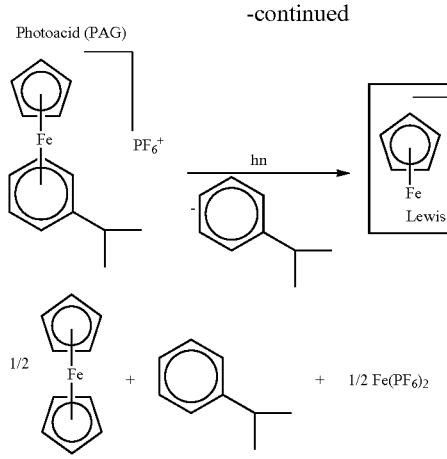

4. poly(HEMA-r-MMA-r-MAA): Poly(Hydroxyethyl methacrylate-r-Methylmethacrylate-r-Methacrylic Acid). MAA is incorporated in order to make the polymer responsive to various pH conditions which can be used to make a smart drug-delivery system.

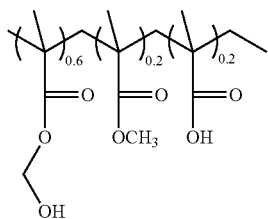

5. PHEMA-PPy. The polymer mixture was formed by hydroxyethylmethacrylate (HEMA), the crosslinker etraethyleneglycol diacrylate (TEGDA), the photoinitiator dimethoxyphenyl acetophenone (DMPA), pyrrole monomer and the enzyme.

6. HEMA-DHPMA with VP. Copolymer of hydroxyethyl methacrylate (HEMA) and 2,3-dihydroxypropyl methacrylate (DHPMA). The porosity and mechanical properties of the hydrogels were improved using N-vinyl-2-pyrrolidinone (VP) as structural strengthener and ethyleneglycol dimethacrylate (EGDMA) as cross-linker.

Methacrylated Derivitized Polymers:

1. Met-HA. Methacrylate derivatized hyaluronic acid.

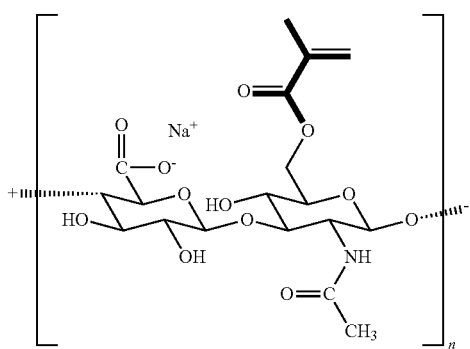

2. Met-PG. Methacrylated Hyperbranched Polyglycerol

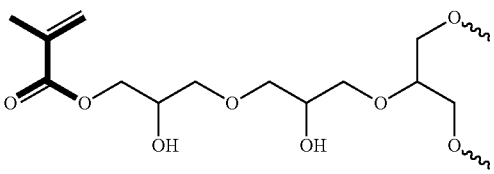

Example of Polyvinyl Alcohol PVA-Based Hydrogel

1. Photoactive PVA. A water based solution of PVA with ammonium dichromate is a negative photoresist.

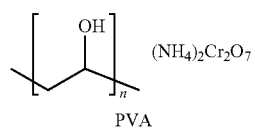

2. Acrylated-PVA. Aqueous solutions of PVA modified by reaction with methacrylamido-acetaldehyde dimethyl acetal to derivatize the PVA with crosslinkable side groups.

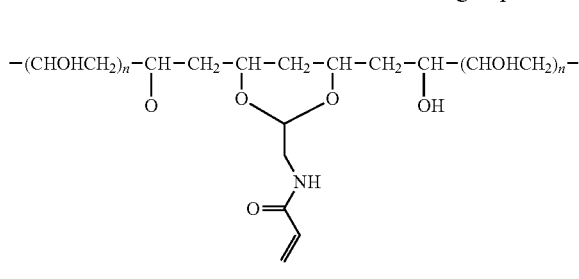

3. PPy-PVA. PVA films exposed to a solutions of Pyrrol.

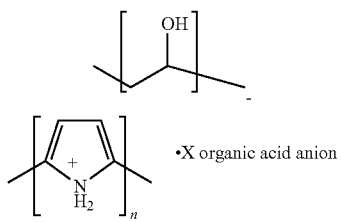

Example of Poly(Ethylene Glycol) PEG

Polyethylene glycol, with its hydroxyl moieties can be acrylated to polyethylene glycol diacrylate (PEG-DA) or polyethylene glycol methyl diacrylate. Acrylate monomers are esters containing vinyl groups directly bonded to the carbonyl atom. A mixture of PEG-DA, with an appropriate molecular weight, and photoinitiator (e.g., Darocure 1173) under UV exposure forms an insoluble three dimensional polymer network, hydrogel membrane. In particular, the photoinitiator generates a photofragment that starts the polymerization by attaching the double CC bond in the acrylate moieties.

Copolymerization of multiple different hydrogel precursors, either by use of co-polymers in the precursor itself or by random co-polymerization during lithographic process, provides an additional degree of flexibility in the choice of the appropriate hydrogel membrane photo-definable.

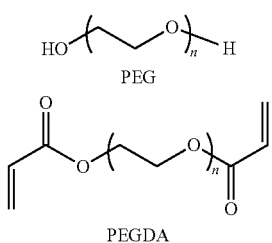

PEG

PEGDA

Polyphosphazenes

Polyphosphazenes represent a highly tailorable class of polymers that possess a phosphorus-nitrogen backbone. Several water-soluble polyphosphazenes have been prepared that can be covalently or ionically cross-linked to form hydrogels. The utility of polyphosphazene hydrogels as platforms for enzyme and cell immobilization on a macroscale has also been demonstrated. In particular, polyphosphazenes with alkyl ether and cinnamyl side groups for hydrogel formation via UV photolithography are investigated for enzyme immobilization in use in a range of microscale enzyme based biosensors.

1. MEEP. A poly[bis(methoxyethoxyethoxy)phosphazene] Solutions.

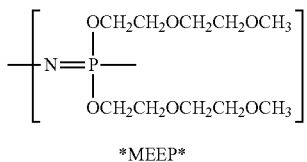

*MEEP*

2. Polyphosphazenes with Cinnamyl Side Groups.

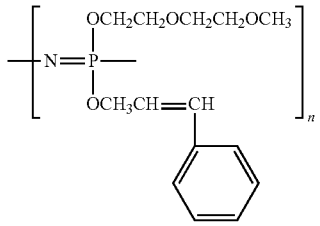

The biosensor of the present example may comprise an adhesive layer for bonding the first photo-definable hydrogel membrane to the foil. The adhesive layer can, for example, be a silane-based adhesive layer. It can comprise an organosilane agent with two functionalities: a hydrolyzable group, typically alkoxy, acyloxy, halogen or amine (linkable to inorganic substrate), and an organofunctional group (linkable to organic deposited layer):

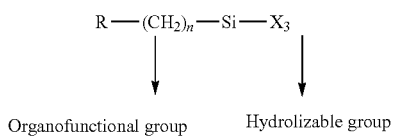

Organofunctional group     Hydrolizable group

In particular, for methacrylate and acrylate hydrogel membranes, the substrate surface is modified with an organosilane to create surface-tethered methacrylate or acrylate groups capable of covalent bonding with a hydrogel during photopolymerization, overcoming the problem of lift off of a hydrogel submerged in water or buffer solution. Methacrylate or acrylate moieties on the foil surface, in fact, participate in the free radical polymerization and create covalent bonding between acrylate groups present in the bulk gel and those on the surface, thus fixing the hydrogel structures to the foil.

Examples of suitable organosilanes include:

acrylate and methacrylate silanes, such as N-(3-acryloxy-2-hydroxypropyl)-3-aminopropyltriethoxysilane, [3-(methacryloyoxy)propyl]trimethoxysilane, 3-(acryloxypropyl)trimethoxysilane, N-(3-acryloxy-2-hydroxypropyl)-3-aminopropyltriethoxysilane, O-(methacryloxyethyl)-N-(triethoxy-silylpropyl)urethane, N-(3-methacryloxy-2-hydroxypropyl)-3-aminopropyltriethoxysilane, methacryloxymethyltriethoxysilane, methacryloxymethyltrimethoxysilane, methacryloxypropyltriethoxysilane, (3-acryloxypropyl)methyldimethoxysilane, (methacryloxymethyl)methyl-diethoxysilane, (methacryloxymethyl)methyl-dimethoxysilane, methacryloxypropylmethyldiethoxysilane, methacryloxypropylmethyldimethoxysilane, methacryloxypropyldimethylethoxysilane, methacryloxypropyldimethyl-methoxysilane;

cyclic azasilanes, such as N-allyl-aza-2,2-dimethoxysilacyclopentane, N-aminoethyl-aza-2,2,4-trimethylsilacyclopentane, N-(3-aminopropyl-dimethylsila)aza-2,2-dimethyl-2-silacyclopentane, N-n-butyl-aza-2,2-dimethoxysila-cyclopentane, 2,2-dimethoxy-1,6-diaza-2-silacyclooctane, N-methyl-aza-2,2,4-trimethylsilacyclopentane, 3-(triethoxysilyl)propylsuccinic anhydride.

dipodal amines, such as bis(trimethoxysilylpropyl)urea, bis(methyldiethoxysilylpropyl)amine, bis(methyldimethoxysylilpropyl)-N-methylamine, bis[(3-trimethoxysilyl)propyl]-ethylenediamine, bis[(3-triethoxysilyl)propyl]-urea,bis-(trimethoxysilylpropyl)amine;

amine functional silanes, such as ureidopropyltriethoxysilane, N-(3-triethoxysilylpropyl)-4,5-dihydroimidazole, acetamidopropyltrimethoxysilane, 2-(2-pyridyethyl)thiopropyltri-methoxysilane, 3-(1,3-dimethylbutyldene)amino-propyltriethoxysilane, ureidopropyltrimethoxysilane, N,N-dioctyl-N'-triethoxysilylpropyl-urea;

carboxylate silanes, such as carboxyethylsilanetriol sodium salt, triethoxysilylpropylmaleamic acid, N-(trimethoxysilylpropyl)ethylene-diamine triacetic acid trisodium salt.

In the following, an example of the manufacturing process for a biosensor, according to an embodiment, is described. As shown in FIG. 1 a support substrate 1 is provided. The support substrate 1 may be made of glass or silicon, for example. A flexible polymeric foil 2 acts itself as substrate or it can be placed on the support substrate 1. An electrode layer 3 is formed on the foil 2. The electrode layer 3 may be made of a metal, for example, gold, or a combination thereof, or an electrically conductive polymeric material. A positive photoresist 4 is formed on the electrode layer and exposed to UV irradiation. The UV irradiation is controlled by means of a (dielectric) photomask 5. The metal of the electrode layer 3, if made of a metal, can then be etched in the exposed regions and the photoresist 4 can subsequently be removed. Alternatively, the photoresist 4 can be spin coated onto the foil layer 2, exposed to irradiation and developed, and metal, if the electrode layer 3 is made of a metal, can be deposited in the regions where the photoresist 4 has been removed during development and subsequently the remaining photoresist 4 covering regions where no electrode layer is formed is removed.

For example, in fabricating the electrode layer 3 in the form of a gold array, a 20 nm Ti seed layer and an 80 nm Au layer are formed via e-beam on the flexible foil 2 based on PEN, commercial Teonex Q83. A positive photoresist is spin coated at 4000 rpm for 30 s. The photoresist is pre-baked for 2 minute at 85° C. Successively, using a mask aligner in hard contact modality, the resist is exposed to UV light at 365 nm at 15 mW/cm$^2$ for 3 s. A Developer solution is used to remove the un-patterned photoresist. Successively, wet etching treatments based on Au and Ti etchant solutions, respectively, are used to remove the gold and seed layers in order to obtain an array of several working microelectrodes patterned on PEN.

Figure 2:
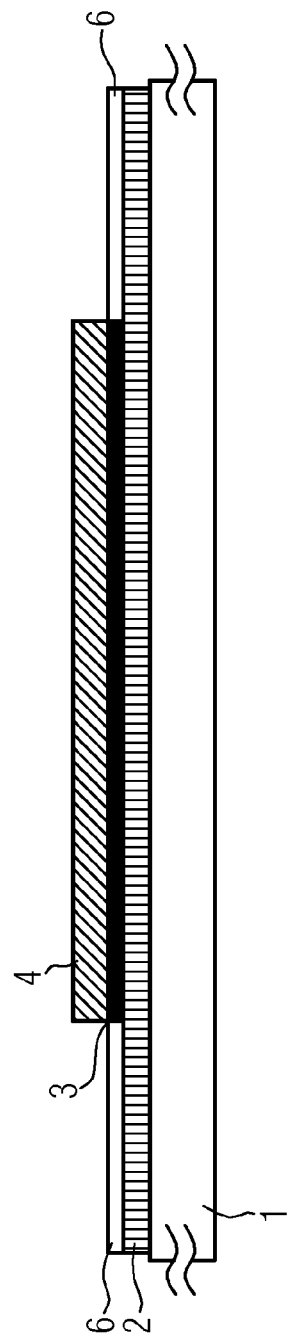
FIG. 2 illustrates a later state of processing of a biosensor according to the example of FIG. 1, wherein a silane adhesive layer is formed.

As shown in FIG. 2 an adhesive layer 6 is formed adjacent to the remaining electrode layer 3 while the photoresist 4 is maintained on top of the electrode layer 3. By provision of the adhesive layer 6 adhesion of a subsequently formed first photo-definable hydrogel membrane to the foil can be significantly enhanced. As already described above, the formation of the adhesive layer 6 on the foil 2 can include plasma treating, in particular, $O_2$ plasma treating, of the foil 2 (with the electrode layer 3 present), immersing the foil 2 in a silane solution (prepared by hydrolysis and condensation of silane-oligomers, for example), rinsing the foil 2 in a solvent and forming a reliable foil-silane bond by heating the structure with the foil 2 and the silane adhesive layer 6.

According to an embodiment, the adhesive layer 6 is formed on the foil 2 as follows. For the flexible foil it is chosen Teonex Q83. The foil 2 with the electrode layer 3 present is treated by $O_2$ plasma etching. In parallel, a silane solution (2% v/v) is prepared with 3-(Trimethoxysilyl)propyl methacrylate in isopropylic alcohol then adjusting pH to 4.5-5 with Acetic acid. The solution might turn somewhat cloudy. In this case, one has to wait for about 30 minutes before applying it in order to allow the hydrolysis of the silanoxe group. The foil 2 with the electrode layer 3 is dipped in the silane solution for 5 minutes and, then, rinsed in isopropylic alcohol and afterwards placed on a hotplate at T=120° C. for 60 minutes to create free methacrylate groups on the substrate. The existence of the silane adhesion layer 6 on the flexible foil 2 can be confirmed by a decrease of contact angle from about 90° to about 68° after silanization.

Figure 3:
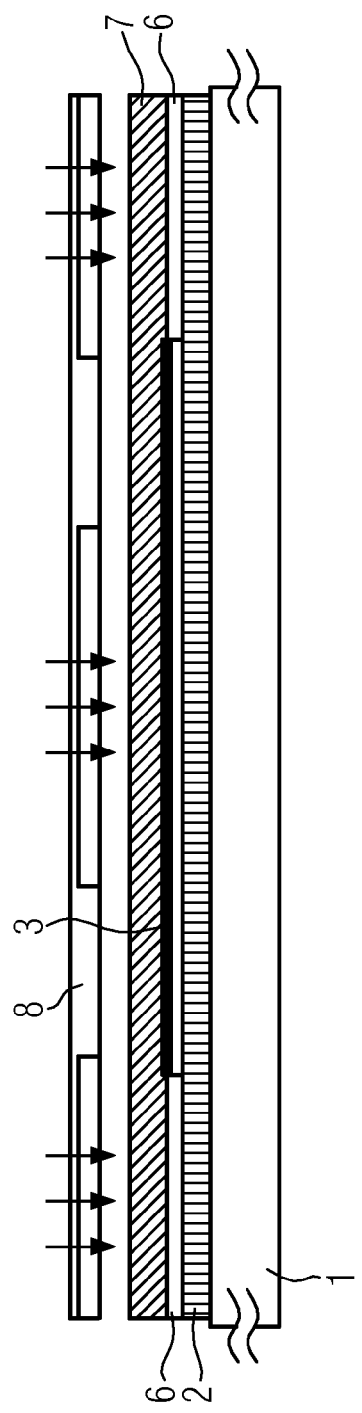
FIG. 3 illustrates a state of processing of a biosensor according to the example of FIG. 1, wherein a first photo-definable hydrogel membrane is formed.

After formation of the adhesive layer 6 on the foil 2 the photoresist 4 is removed. After removal of the photoresist 4 from the electrode layer 3 a first photo-definable hydrogel membrane 7 (isolation membrane) is formed on the electrode layer 3 and the adhesive layer 6 as it is shown in FIG. 3. The first photo-definable hydrogel membrane 7 is lithographically patterned by means of a photomask 8 in order to isolate an electrode (sensing electrode of the finished product), pads and vias, for example, from the electrode layer 3. Regions of the first photo-definable hydrogel membrane 7 that are exposed by the (windows of the) photomask 8 are irradiated by UV radiation in order to open windows for the electrode and pads, etc. Subsequently, development in water is performed to remove unexposed regions of the first photo-definable hydrogel membrane 7.

According to an example, the first photo-definable hydrogel membrane 7 is formed as follows. A prepolymer of photo-definable hydrogel membrane is prepared by adding 2% of photoinitiator (2-hydroxy-2-methylpropiophenone) to PEG-DA. A PEG-DA prepolymer solution is spin-coated at 800 rpm for 10 s onto a Teonex Q83 foil 2 with gold electrode layer 3. The photomask 8 is aligned with the electrode pattern 3 and exposed to UV light 365 nm at 15 mW/cm$^2$ for 30 s. The prepolymer is converted into cross-linked photo-definable hydrogel. The unpolymerized membrane is removed in a wash of deionized water within a few minutes.

Figure 4A:
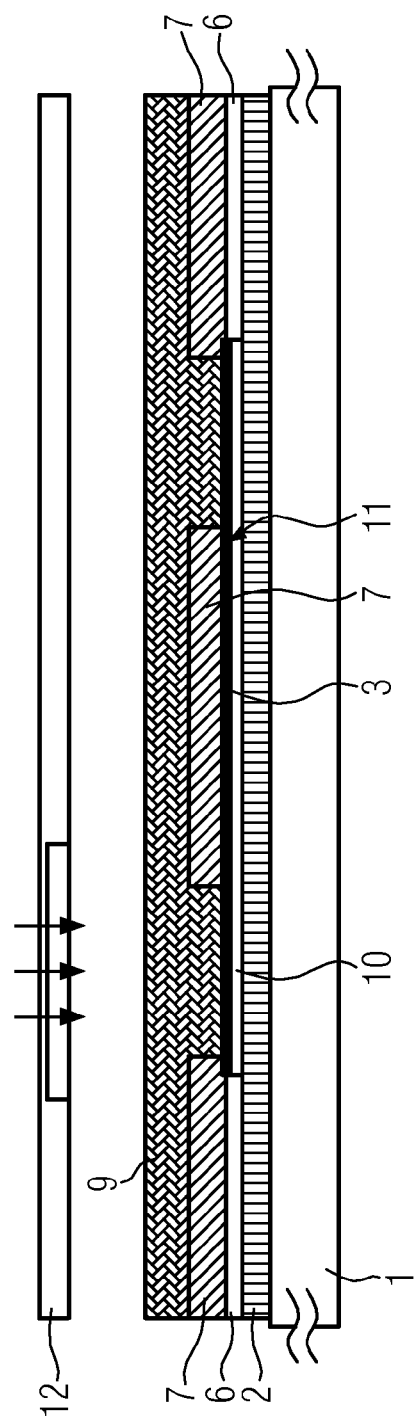
FIG. 4a illustrates a state of processing of a biosensor according to the example of FIG. 1, wherein a second photo-definable hydrogel membrane with an immobilized bio-recognition element is formed according to a first alternative.

As a next step in the illustrative example for manufacturing a biosensor according to the disclosure, a second photo-definable hydrogel membrane 9 with an immobilized bio-recognition element is formed as it is shown in FIGS. 4a and 4b.

According to the example shown in FIG. 4a the second bioactive photo-definable hydrogel membrane 9 is spin-coated on the remaining parts of the first photo-definable hydrogel membrane 7 and the exposed portions of the electrode layer 3 (in particular, the electrode). One of the exposed portions of the electrode layer 3 will function as an electrode 10 whereas another one will function as a pad 11. The second bioactive photo-definable hydrogel membrane 9 shown in FIG. 4a is photolithographically structured by means of a photomask 12. For this, a portion of the second bioactive photo-definable hydrogel membrane 9 exposed by the photomask 12 is irradiated by UV radiation and the non-exposed portions are subsequently removed by development of the structure in water. By the UV radiation a bio-recognition element as, for example, an enzyme, is immobilized in the second bioactive photo-definable hydrogel membrane 9 without denaturizing the enzyme.

According to an example the second bioactive photo-definable hydrogel membrane 9 with a bio-recognition element, for example, an enzyme, is deposited as follows. A solution of enzyme is dissolved in a PBS buffer and glutaraldehyde. Enzyme is added at 20% (v/v) to a prepolymer that has been prepared by adding 2% of photoinitiator to PEG-DA and vinylferrocene. The mix is stirred for 4-5 h at 45 degrees C. to homogenize the enzyme. The solution is spin coated at 800 rpm for 10 s on the surface of the Teonex foil 2 over the patterned electrode layer 3 and the first photo-definable hydrogel membrane 7 (isolation membrane) that was previously patterned. The photomask 12 is aligned with the electrode 10 and exposed to UV light (365 nm) at 15 mW/cm$^2$ for 30 s. The prepolymer is converted into a cross-linked photo-definable hydrogel. The unpolymerized membrane is removed in a wash of deionized water for a few minutes.

In an alternative approach and as shown in FIG. 4b the second bioactive photo-definable hydrogel membrane 9 is not formed by spin-coating but rather ink-jet printed on the exposed electrode 10 in a manner overlapping adjacent portions of the first photo-definable hydrogel membrane 7. According to an embodiment, the second hydrogel membrane 9 is closely patterned during the printing process, and thus does not require further patterning. Therefore, the entire biosensor structure is exposed to UV radiation to polymerize the second hydrogel membrane 9, without the requirement of a photo mask.

According to an alternative embodiment, during the printing process, the second hydrogel membrane 9 is deposited over a general region that includes the electrode 10. A photomask 12 is then aligned, and the unmasked portion of the second hydrogel membrane 9 is exposed as previously described, to more precisely define the region directly over the electrode 10.

After formation of the second bioactive photo-definable hydrogel membrane 9, by any appropriate method, including spin-coating and photolithographic structuring or by inkjetting, the support substrate 1 is removed and the resulting structure shown in FIG. 5 is available for finish-processing (contacting, etc.).

All previously discussed embodiments are not intended as limitations but serve as examples illustrating features and advantages of the disclosure. It is to be understood that some or all of the above described features can also be combined in different ways to provide further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
   a foil layer;
   an electrode layer positioned on the foil layer;
   a first hydrogel layer positioned over the foil layer and having an opening through which a portion of the electrode layer is exposed; and
   a second hydrogel layer positioned in the opening and in contact with the electrode layer, the second hydrogel layer including an immobilized bio-recognition element.

2. The device of claim 1, further comprising:
   an adhesive layer positioned between and in contact with the foil layer and the first hydrogel layer.

3. The device of claim 1, wherein the opening in the first hydrogel layer is one of a plurality of openings in the first hydrogel layer through which respective portions of the electrode layer are exposed, and wherein the second hydrogel layer is in contact with the electrode layer through fewer than all of the plurality of openings in the first hydrogel layer.

4. The device of claim 1, wherein the foil layer is a polymeric foil.

5. The device of claim 1, wherein the electrode layer is a layer of an electrically conductive polymer.

6. The device of claim 1, wherein the electrode layer comprises a titanium seed layer in contact with the foil layer and a gold layer positioned over the titanium seed layer.

7. A biosensor, comprising:
   a substrate;
   an electrode layer over the substrate;
   a first hydrogel layer positioned over the substrate and having a through-opening extending to the electrode layer; and
   a second hydrogel layer positioned in the opening and in contact with the electrode layer, the second hydrogel layer including an immobilized bio-recognition element.

8. The biosensor of claim 7, wherein the second hydrogel layer is arranged partly on and in direct contact with the first hydrogel layer and partly on and in direct contact with the electrode layer.

9. The biosensor of claim 7, wherein the second hydrogel layer includes a first portion positioned in the opening and in contact with the electrode layer and a second portion positioned on the first hydrogel layer such that the first hydrogel layer is positioned between the second portion of the second hydrogel layer and the electrode layer.

10. The biosensor of claim 7, further comprising:
    a foil layer positioned on the substrate; and
    an adhesive layer positioned over and in contact with the foil layer and between a part of the first hydrogel layer and the foil layer.

11. The biosensor of claim 10, wherein the adhesive layer comprises silane.

12. The biosensor of claim 7, wherein the bio-recognition element is an enzyme.

13. The biosensor of claim 7, wherein at least one of the first and second photo-definable hydrogel membranes comprises at least one of oligomers and prepolymers.

14. The biosensor of claim 13, wherein the at least one of oligomers and prepolymers is selected from a group consisting of:

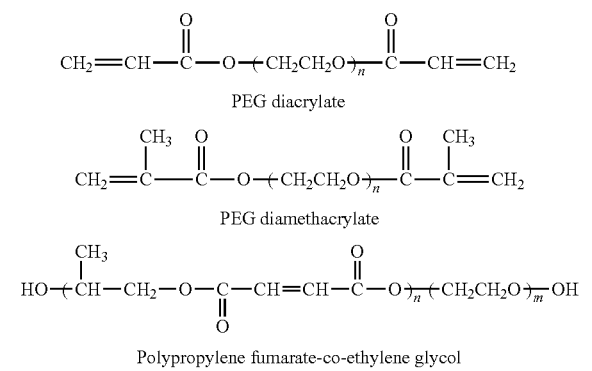

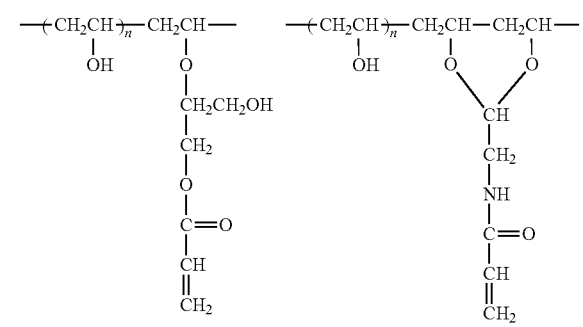

-continued

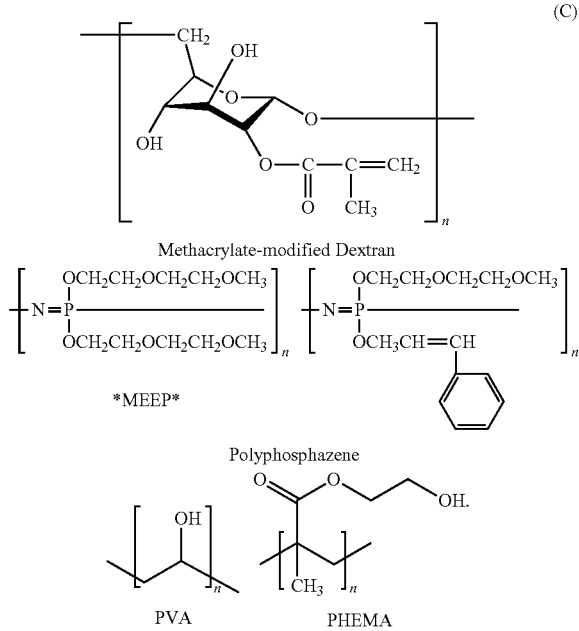

15. A biosensor, comprising
a substrate;
an electrode layer over the substrate;
a first hydrogel layer positioned over the substrate and having a through-opening extending to the electrode layer; and
a second hydrogel layer positioned in the opening and in contact with the electrode layer, the second hydrogel layer including an immobilized bio-recognition element, wherein a portion of the first hydrogel layer is positioned between a portion of the second hydrogel layer and the electrode layer.

16. The biosensor of claim 15, wherein the second hydrogel layer is arranged partly on and in direct contact with the first hydrogel layer and partly on and in direct contact with the electrode layer.

17. The biosensor of claim 15, wherein the second hydrogel layer includes a first portion positioned in the opening and in contact with the electrode layer and a second portion positioned on the first hydrogel layer such that the first hydrogel layer is positioned between the second portion of the second hydrogel layer and the electrode layer.

18. The biosensor of claim 15, further comprising:
a foil layer positioned on the substrate; and
an adhesive layer positioned over and in contact with the foil layer and between a part of the first hydrogel layer and the foil layer.

19. The biosensor of claim 15, wherein the bio-recognition element is an enzyme.

20. The biosensor of claim 15, wherein at least one of the first and second photo-definable hydrogel membranes comprises at least one of oligomers and prepolymers selected from a group consisting of PEG diacrylate, PEG diamethacrylate, polyproplylene fumerate-co-ethylene glycol, acrylic modified PVA, commutated hyaluronic acid, methacrylate-modified Dextran, and polyphosphazene.

* * * * *